United States Patent [19]
Shin

[11] Patent Number: 4,511,716
[45] Date of Patent: * Apr. 16, 1985

[54] METHOD OF PREPARING ADENINE

[75] Inventor: Kju H. Shin, Baton Rouge, La.

[73] Assignee: Ethyl Corporation, Richmond, Va.

[*] Notice: The portion of the term of this patent subsequent to Jul. 5, 2000 has been disclaimed.

[21] Appl. No.: 463,962

[22] Filed: Feb. 4, 1983

Related U.S. Application Data

[63] Continuation-in-part of Ser. No. 357,009, Mar. 11, 1982, abandoned.

[51] Int. Cl.$^3$ .............................................. C07D 432/32
[52] U.S. Cl. .................................................... 544/277
[58] Field of Search ........................ 544/277; 424/253

[56] References Cited

U.S. PATENT DOCUMENTS 4,391,977 12/1981 Shin ..................................... 544/277

Primary Examiner—Nicholas S. Rizzo
Attorney, Agent, or Firm—Donald L. Johnson; John F. Sieberth; Patricia J. Hogan

[57] ABSTRACT

In the preparation of adenine from hydrogen cyanide, formamide, an ammonium salt, and methyldisulfide, the formation of a polymer by-product is reduced by heating a reaction mixture comprising the formamide and ammonium salt in a closed vessel to a reaction temperature of about 50°–180° C., adding the hydrogen cyanide to the preheated mixture over a period of about 1–5 hours, and maintaining the reaction temperature until the reaction is complete.

10 Claims, No Drawings

METHOD OF PREPARING ADENINE

CROSS-REFERENCE

This application is a continuation-in-part of copending application Ser. No. 357,009, filed Mar. 11, 1982, now abandoned.

FIELD OF INVENTION

This invention relates to adenine and more particularly relates to a method of reducing polymer formation in the synthesis of adenine.

BACKGROUND

As evidenced by U.S. Pat. Nos. 3,287,452, 3,398,149, 3,427,315, 3,671,649, 4,059,582, and 4,092,314 and Japanese Patent Publication Nos. 42-7915 and 51-26897, there are several known methods of preparing adenine. A particularly attractive method—a simple, one-step process for preparing adenine by reacting hydrogen cyanide with formamide in the presence of an ammonium salt and a catalytic amount of methyldisulfide at elevated temperatures—is taught in application Ser. No. 331,036 (Shin), filed Dec. 16, 1981, now U.S. Pat. No. 4,391,977. This process generally provides adenine in good yields but has the disadvantage of leading to the formation of a black polymer by-product which may constitute about 7–62% of the total product. The polymer formation, which results from the exothermic nature of the reaction, decreases adenine yields and leads to filtration difficulties, material losses on the filter and in solids handling, and increased operating and equipment costs.

SUMMARY OF INVENTION

An object of this invention is to provide a novel process for preparing adenine.

Another object is to provide such a process wherein the adenine is synthesized from hydrogen cyanide, formamide, an ammonium salt, and methyldisulfide.

A further object is to provide such a process wherein polymer formation is minimized.

These and other objects are attained by conducting the synthesis of adenine from hydrogen cyanide, formamide, an ammonium salt, and methyldisulfide by (1) heating a reaction mixture comprising formamide and an ammonium salt in a closed vessel to a reaction temperature of about 50°–180° C., (2) adding the hydrogen cyanide to the preheated mixture over a period of about 1–5 hours, and (3) maintaining the reaction temperature until the reaction is complete.

DETAILED DESCRIPTION

The hydrogen cyanide used in the practice of the invention is anhydrous hydrogen cyanide, which may be in liquid or gaseous form.

The formamide of the reaction mixture is both a reactant and a reaction medium and is therefore used in excess, i.e., up to about 20 mols of formamide per mol of hydrogen cyanide. Optimally, the amount of formamide employed is about 5 mols per mol of hydrogen cyanide.

The ammonium salt of the invention may be the ammonium salt of any inorganic or organic acid, and it may be incorporated per se or generated in situ. Thus, for example, it may be an acetate, sulfate, iodide, chloride, carbonate, propionate, benzoate, nitrate, etc.; and it may be incorporated as the ammonium salt or its progenitors. The preferred ammonium salt is ammonium acetate, which may be incorporated as ammonium acetate or as a 1:1 molar mixture of gaseous ammonia and acetic acid which will generate the ammonium acetate in situ. In general, the amount of ammonium salt employed is about 0.5–3, preferably about 0.66, mols per mol of hydrogen cyanide.

The methyldisulfide is employed in a catalytic amount, preferably about 0.5–4 mols per mol of hydrogen cyanide. It may be incorporated at any convenient time, i.e., together with the formamide and ammonium salt, together with the hydrogen cyanide, or partially together with the formamide and ammonium salt and partially together with the hydrogen cyanide. However, it is preferably incorporated together with the hydrogen cyanide.

As indicated above, the process of the invention is conducted by gradually adding hydrogen cyanide and, optionally, the methyldisulfide to a preheated mixture of the formamide, ammonium salt, and, optionally, the methyldisulfide. Ordinarily, this gradual addition is accomplished incrementally, but a continuous addition is also feasible.

The process of the invention leads to the production of adenine in good yields, with polymer formation reduced to levels typically in the range of about 3–5.5% of the total product. The most preferred and advantageous results are achieved when the process is conducted by (1) introducing a mixture of the formamide and ammonium salt into a suitable pressure-resistant vessel, (2) heating the contents of the vessel to a temperature of about 130° C., (3) maintaining this temperature for about 0.5–1 hour, (4) lowering the temperature to about 80° C., (5) gradually adding a mixture of hydrogen cyanide and methyldisulfide under nitrogen pressure, either continuously or incrementally, over a period of about 1–5, typically 3, hours, (6) increasing the temperature, e.g., to about 130° C., and (7) maintaining this temperature for a period of time, e.g., up to about 3 hours, sufficient for the reaction to go to completion. A maximum yield of 32.4% adenine and a minimum yield of 3.5% polymer has been obtained by this procedure.

Experiments have shown that feeding hydrogen cyanide into a reaction mixture of formamide and ammonium salt having a temperature substantially in excess of 80° C. results in a decreased adenine production, i.e., 21.5–27.5% of the product mixture, although polymer formation remains very low, i.e., 3.2–4.1%. However, reducing the temperature of the initial reaction mixture to temperatures substantially below 80° C. results not only in decreasing the adenine yield to about 29.4% but in increasing the amount of polymer formed to about 10.2% of the reaction mixture. It is therefore apparent that the temperature of the reaction mixture into which the hydrogen cyanide is introduced is an important process variable.

The following examples are given to illustrate the invention and are not intended as a limitation thereof.

EXAMPLE I

A suitable autoclave was charged with 4.8 molar proportions of formamide and 0.6 molar proportion of ammonium acetate, heated to 130° C., and maintained at that temperature for one hour. The mixture was then cooled to 80° C. and maintained at that temperature while a mixture of one molar proportion of liquid hydrogen cyanide and 0.4 molar proportion of methyldisulfide was added under nitrogen pressure in a series of equal increments over a period of three hours, and the resultant mixture was reacted for another three hours. The temperature was then raised to 130° C. for an additional three hours of reaction, after which the autoclave was cooled, gas was vented through a caustic scrubber, and the mixture was discharged. Analysis by HPLC showed that the process resulted in a 32.4% yield of adenine, an 0.2% yield of 4,5-dicyanoimidazole, a 2.1% yield of diaminiomaleonitrile, and a 3.5% yield of polymer.

EXAMPLE II

Example I was repeated except that the reaction mixture was cooled to 100° C. rather than 80° C. prior to the addition of the hydrogen cyanide/methyldisulfide mixture and maintained at that temperature until it was elevated to 130° C. for the final three hours of the reaction. HPLC analysis showed a 27.5% yield of adenine, an 0.8% yield of dicyanoimidazole, a 4.5% yield of diaminomaleonitrile, and a 10.2% yield of polymer.

EXAMPLE III

Example I was repeated except that the amount of formamide was reduced to 4.4 molar proportions, and the temperature was maintained at 130° C. thoughout the reaction instead of being reduced to 80° C. prior to the addition of the hydrogen cyanide/methyldisulfide mixture. HPLC analysis showed a 21.5% yield of adenine, an 2.85% yield of 4,5-dicyanoimidazole, a 1.07% yield of diaminomaleonitrile, and a 4.1% yield of polymer.

EXAMPLE IV

A suitable autoclave was charged with a mixture of 4.9 molar proportions of formamide, 0.6 molar proportion of ammonium acetate, and 0.5 molar proportion of methyldisulfide, heated to 130° C., and maintained at that temperature for one hour. Then one molar proportion of liquid hydrogen cyanide was added under nitrogen pressure in a series of equal increments over a period of three hours while the temperature was maintained at 130° C., and that temperature was maintained for an additional three hours of reaction. After the reaction, the autocalve was cooled, the gas was vented through a caustic scrubber, and the mixture was discharged. HPLC analysis showed a 22.0% yield of adenine, a 2.3% yield of 4,5-dicyanoimidazole, an 0.5% yield of diaminomaleonitrile, and a 3.7% yield of polymer.

EXAMPLE V

A suitable autoclave was charged with a mixture of 4.7 molar proportions of formamide and 0.6 molar proportion of ammonium acetate and heated at 130° C. for one hour. The temperature was then reduced to 60° C. and not raised until a mixture of one molar proportion of liquid hydrogen cyanide and 0.4 molar proportion of methyldisulfide was added under nitrogen pressure in a series of equal increments over a period of three hours. The resultant reaction mixture was then heated at 130° C. for an additional three hours, after which the autoclave was cooled, gas was vented through a caustic scrubber, and the mixture was discharged. HPLC analysis showed a 29.4% yield of adenine, an 0.2% yield of 4,5-dicyanoimidazole, a 4.5% yield of diaminomaleonitrile, and a 10.2% yield of polymer.

EXAMPLE VI

A suitable autoclave was charged with a mixture of 4.9 molar proportions of formamide and 0.7 molar proportion of ammonium acetate and heated to 80° C. That temperature was maintained while a mixture of one molar proportion of liquid hydrogen cyanide and 0.4 molar proportion of methyldisulfide was added under nitrogen pressure in a series of equal increments over a period of three hours, and the resultant mixture was allowed to react for an additional 20 hours. The autoclave was cooled, the gas vented through a caustic scrubber, and the product mixture discharged. HPLC analysis showed a 30.9% yield of adenine, an 0.1% yield of 4,5-dicyanoimidazole, a 6.8% yield of diaminomaleonitrile, and a 5.3% yield of polymer.

It is obvious that many variations may be made in the products and processes set forth above without departing from the spirit and scope of this invention.

I claim:

1. In a process for preparing adenine by the reaction of hydrogen cyanide, formamide, an ammonium salt, and methyldisulfide, the improvement which comprises (1) heating a reaction mixture comprising the formamide and ammonium salt in a closed vessel to a reaction temperature of about 50°–180° C., (2) adding the hydrogen cyanide to the preheated mixture over a period of about 1–5 hours, and (3) maintaining the reaction temperature until the reaction is complete.

2. The process of claim 1 wherein the hydrogen cyanide is added to the reaction mixture incrementally.

3. The process of claim 1 wherein the methyldisulfide is incorporated into the initial reaction mixture.

4. The process of claim 1 wherein the methyldisulfide is incorporated into the reaction mixture together with the hydrogen cyanide.

5. The process of claim 1 wherein the amount of formamide employed is about 2–20 mols per mol of hydrogen cyanide.

6. The process of claim 1 wherein the amount of ammonium salt employed is about 0.5–3 mols per mol of hydrogen cyanide.

7. The process of claim 1 wherein the ammonium salt is an acetate, sulfate, iodide, chloride, carbonate, propionate, benzoate, or nitrate.

8. The process of claim 1 wherein the ammonium salt is generated in situ from gaseous ammonia and the corresponding inorganic or organic acid.

9. The process of claim 1 wherein the amount of methyldisulfide employed is about 0.5–4 mols per mol of hydrogen cyanide.

10. The process of claim 1 which comprises (1) heating a mixture of formamide and an ammonium salt in a closed vessel to a temperature of about 130° C., (2) maintaining the reaction mixture at this temperature for about 0.5–1 hour, (3) lowering the temperature to about 80° C., (4) incrementally adding a mixture of hydrogen cyanide and methyldisulfide to the reaction mixture over a period of about 1–5 hours while maintaining the temperature at about 80° C., (5) increasing the temperature to about 130° C., and (6) maintaining the reaction mixture at the higher temperature until the reaction is complete.

* * * * *